US00RE46582E

(19) United States
(12) Reissued Patent
Morgan et al.

(10) Patent Number: US RE46,582 E
(45) Date of Reissued Patent: Oct. 24, 2017

(54) ORTHOPAEDIC IMPLANT WITH SENSORS

(71) Applicant: DePuy Synthes Products, Inc., Raynham, MA (US)

(72) Inventors: Chad Morgan, West Grove, PA (US); Harry T. Hall, Downingtown, PA (US); James M. Green, Portland, OR (US); Geoffrey Flexner, Chester Springs, PA (US); Charles E. Geltz, Drexel Hill, PA (US)

(73) Assignee: DEPUY SYNTHES PRODUCTS, INC., Raynham, MA (US)

(21) Appl. No.: 14/844,768

(22) Filed: Sep. 3, 2015

Related U.S. Patent Documents

Reissue of:
(64) Patent No.: 8,551,092
Issued: Oct. 8, 2013
Appl. No.: 13/298,808
Filed: Nov. 17, 2011

U.S. Applications:
(63) Continuation of application No. 11/147,750, filed on Jun. 7, 2005, now Pat. No. 8,083,741.

(60) Provisional application No. 60/578,107, filed on Jun. 7, 2004.

(51) Int. Cl.
*A61B 17/56* (2006.01)
*A61B 17/68* (2006.01)

(52) U.S. Cl.
CPC ..... *A61B 17/68* (2013.01)

(58) Field of Classification Search
CPC ..... A61F 2002/4666; A61B 17/60; A61B 2017/681
USPC ..... 606/53, 60, 57, 90, 105, 282
See application file for complete search history.

(56) References Cited

U.S. PATENT DOCUMENTS

| | | | |
|---|---|---|---|
| 3,646,940 | A | 3/1972 | Timm et al. |
| 3,745,995 | A | 7/1973 | Kraus |
| 3,783,880 | A | 1/1974 | Kraus |
| 3,788,647 | A | 1/1974 | Evans et al. |
| 3,820,534 | A | 6/1974 | Kraus |
| 3,842,841 | A | 10/1974 | Brighton et al. |
| 3,918,440 | A | 11/1975 | Kraus |
| 3,922,918 | A | 12/1975 | Farrar, Jr. et al. |

(Continued)

FOREIGN PATENT DOCUMENTS

| | | |
|---|---|---|
| CH | 662279 | 9/1987 |
| DE | 3245453 | 9/1984 |

(Continued)

*Primary Examiner* — Beverly M Flanagan
(74) *Attorney, Agent, or Firm* — Fay Kaplun & Marcin, LLP

(57) ABSTRACT

A monitoring system includes: (1) an implant having at least one sensor and configured for at least partial insertion into a patient, a first one of sensors being in contact with a perimeter of a hole in a body portion of the implant for accepting a fastener; (2) a microchip associated with the implant and the sensor, the microchip configured to receive at least a first signal from the sensor; (3) a transmitter associated with the microchip for transmitting a second signal, representative of the first signal; (4) a receiver located outside of the patient, the receiver configured receive the transmitted second signal; and (5) a display device associated with the receiver, the display device configured to provide an audible or visual representation of the second signal to a user.

26 Claims, 10 Drawing Sheets

(56) References Cited

U.S. PATENT DOCUMENTS 3,964,473 A 6/1976 Wickham et al.
3,977,391 A 8/1976 Fleischmann
4,006,735 A 2/1977 Hittman et al.
4,014,319 A 3/1977 Favre
4,026,276 A 5/1977 Chubbuck
4,026,304 A 5/1977 Levy
4,027,661 A 6/1977 Lyon et al.
4,062,354 A 12/1977 Taylor et al.
4,114,606 A 9/1978 Seylar
4,127,110 A 11/1978 Bullara
4,141,349 A 2/1979 Ory et al.
4,153,060 A 5/1979 Korostoff et al.
4,186,749 A 2/1980 Fryer
4,195,367 A 4/1980 Kraus
4,214,322 A 7/1980 Kraus
4,216,548 A 8/1980 Kraus
4,231,376 A 11/1980 Lyon et al.
4,246,908 A 1/1981 Inagaki et al.
4,265,252 A 5/1981 Chubbbuck et al.
4,306,564 A 12/1981 Kraus
4,313,438 A 2/1982 Greatbatch
4,314,554 A 2/1982 Greatbatch
4,333,469 A 6/1982 Jeffcoat et al.
4,354,506 A 10/1982 Sakaguchi et al.
4,391,124 A 7/1983 Drost et al.
4,414,979 A 11/1983 Hirshorn et al.
4,421,115 A 12/1983 Kraus
4,432,361 A 2/1984 Christensen et al.
4,506,681 A 3/1985 Mundell
4,549,546 A 10/1985 Kelley et al.
4,549,547 A 10/1985 Brighton et al.
4,558,701 A 12/1985 Spalten
4,576,158 A 3/1986 Boland
4,602,638 A 7/1986 Adams
4,611,597 A 9/1986 Kraus
4,618,822 A 10/1986 Hansen
4,665,920 A 5/1987 Campbell
4,738,267 A 4/1988 Lazorthes et al.
4,784,154 A 11/1988 Shirley et al.
4,869,265 A 9/1989 McEwen
4,993,428 A 2/1991 Arms
5,024,239 A 6/1991 Rosenstein
5,030,236 A 7/1991 Dean
5,037,442 A 8/1991 Wintermantel et al.
5,052,375 A 10/1991 Stark et al.
5,056,518 A 10/1991 Pethica et al.
5,056,530 A 10/1991 Butler et al.
5,083,573 A 1/1992 Arms
5,112,332 A * 5/1992 Cozad ..... A61B 17/7008 606/279
5,188,109 A 2/1993 Saito
5,197,488 A 3/1993 Kovacevic
5,263,955 A * 11/1993 Baumgart ..... A61B 17/7216 606/62
5,290,281 A 3/1994 Tschakaloff
5,304,210 A 4/1994 Crook
5,314,458 A 5/1994 Najafi et al.
5,326,363 A 7/1994 Aikins
5,330,477 A 7/1994 Crook
5,360,016 A 11/1994 Kovacevic
5,368,546 A 11/1994 Stark et al.
5,406,853 A 4/1995 Lintilhac et al.
5,425,775 A 6/1995 Kovacevic et al.
5,433,203 A 7/1995 Kimura et al.
5,437,668 A * 8/1995 Aronson ..... A61B 17/62 606/54
5,441,527 A 8/1995 Erickson et al.
5,456,724 A 10/1995 Yen et al.
5,470,354 A 11/1995 Hershberger et al.
5,497,147 A 3/1996 Arms et al.
5,524,624 A 6/1996 Tepper et al.
5,565,005 A 10/1996 Erickson et al.
5,626,579 A 5/1997 Muschler et al.
5,678,448 A 10/1997 Fullen et al.
5,695,496 A 12/1997 Orsak et al.
5,738,521 A 4/1998 Dugot
5,752,976 A 5/1998 Duffin et al.
5,766,231 A 6/1998 Erickson et al.
5,777,467 A 7/1998 Arms et al.
5,791,350 A 8/1998 Morton
5,792,076 A 8/1998 Orsak et al.
5,827,209 A 10/1998 Gross
5,873,840 A 2/1999 Neff
5,887,351 A 3/1999 Arms et al.
5,978,972 A 11/1999 Stewart et al.
6,022,349 A 2/2000 McLeod et al.
6,025,725 A 2/2000 Gershenfeld et al.
6,034,295 A 3/2000 Rehberg et al.
6,034,296 A * 3/2000 Elvin ..... A61B 5/0031 128/903
6,059,784 A 5/2000 Perusek
6,083,174 A 7/2000 Brehmeier-Flick et al.
6,092,530 A 7/2000 Weissman et al.
6,111,520 A 8/2000 Allen et al.
6,112,122 A 8/2000 Schwardt et al.
6,113,553 A 9/2000 Chubbuck
6,117,089 A 9/2000 Sinha
6,120,467 A 9/2000 Schallhorn
6,120,502 A 9/2000 Michelson
6,143,035 A 11/2000 McDowell
6,165,135 A 12/2000 Neff
6,176,879 B1 1/2001 Reischl et al.
6,248,080 B1 6/2001 Miesel et al.
6,261,247 B1 7/2001 Ishikawa et al.
6,278,379 B1 8/2001 Allen et al.
6,289,753 B1 9/2001 Basser et al.
6,292,699 B1 9/2001 Simon et al.
6,305,229 B1 10/2001 Inoue
6,311,562 B1 11/2001 Hanada
6,322,562 B1 11/2001 Wolter
6,357,303 B1 3/2002 Smith et al.
6,387,096 B1 5/2002 Hyde, Jr.
6,433,629 B2 8/2002 Hamel et al.
6,443,891 B1 9/2002 Grevious
6,447,448 B1 9/2002 Ishikawa et al.
6,453,198 B1 9/2002 Torgerson et al.
6,481,440 B2 11/2002 Gielen et al.
6,494,097 B1 12/2002 Shihadeh
6,529,127 B2 3/2003 Townsend et al.
6,533,733 B1 3/2003 Ericson et al.
6,546,293 B2 4/2003 Errico et al.
6,554,781 B1 4/2003 Carter et al.
6,572,543 B1 6/2003 Christopherson et al.
6,575,042 B1 6/2003 Rinner
6,581,481 B1 6/2003 Perusek
6,583,630 B2 6/2003 Mendes et al.
6,585,666 B2 7/2003 Suh et al.
6,591,698 B1 7/2003 Carlsson et al.
6,605,089 B1 8/2003 Michelson
6,610,096 B2 8/2003 MacDonald
6,622,567 B1 9/2003 Hamel et al.
6,636,760 B1 10/2003 Casey et al.
6,638,276 B2 10/2003 Sharkey et al.
6,648,903 B1 11/2003 Pierson, III
6,656,135 B2 12/2003 Zogbi et al.
6,689,087 B2 2/2004 Pal et al.
6,706,005 B2 3/2004 Roy et al.
6,706,042 B2 * 3/2004 Taylor ..... A61B 17/66 606/57
6,802,811 B1 10/2004 Slepian
6,932,308 B2 8/2005 Talish et al.
6,974,417 B2 12/2005 Lockwood et al.
6,976,982 B2 12/2005 Santini et al.
7,007,699 B2 3/2006 Martinelli et al.
7,060,075 B2 6/2006 Govari et al.
7,237,556 B2 7/2007 Smothers et al.
7,357,037 B2 * 4/2008 Hnat ..... A61B 5/0031 73/795
8,241,296 B2 * 8/2012 Wasielewski ..... A61B 17/00 606/96
2001/0000195 A1 4/2001 Smith et al.
2001/0000803 A1 5/2001 Gielen et al.
2001/0047246 A1 11/2001 Fullen et al.
2002/0024450 A1 * 2/2002 Townsend et al. ..... 340/870.16

(56) References Cited

U.S. PATENT DOCUMENTS

| | | | | |
|---|---|---|---|---|
| 2002/0049394 | A1* | 4/2002 | Roy et al. | 600/594 |
| 2002/0050174 | A1 | 5/2002 | Valdevit et al. | |
| 2002/0110715 | A1 | 8/2002 | Schulman et al. | |
| 2002/0111660 | A1 | 8/2002 | Errico et al. | |
| 2002/0115944 | A1 | 8/2002 | Mendes et al. | |
| 2002/0143268 | A1 | 10/2002 | Meredith et al. | |
| 2002/0147416 | A1 | 10/2002 | Zogbi et al. | |
| 2002/0151770 | A1 | 10/2002 | Noll, III et al. | |
| 2002/0198604 | A1 | 12/2002 | Schulman et al. | |
| 2003/0029247 | A1 | 2/2003 | Biedermann et al. | |
| 2003/0032997 | A1 | 2/2003 | Pianca et al. | |
| 2003/0040806 | A1 | 2/2003 | MacDonald | |
| 2003/0055476 | A1 | 3/2003 | Vinup et al. | |
| 2003/0066365 | A1 | 4/2003 | Biermann et al. | |
| 2003/0069623 | A1 | 4/2003 | Stypulkowski | |
| 2003/0069644 | A1 | 4/2003 | Kovacevic et al. | |
| 2003/0078633 | A1 | 4/2003 | Firlik et al. | |
| 2003/0083746 | A1 | 5/2003 | Kuslich | |
| 2003/0088301 | A1 | 5/2003 | King | |
| 2003/0105461 | A1 | 6/2003 | Putnam | |
| 2003/0120323 | A1 | 6/2003 | Meadows et al. | |
| 2003/0135253 | A1 | 7/2003 | Kokones et al. | |
| 2003/0139690 | A1 | 7/2003 | Aebli et al. | |
| 2003/0139782 | A1 | 7/2003 | Duncan et al. | |
| 2003/0153918 | A1 | 8/2003 | Putnam et al. | |
| 2003/0153959 | A1 | 8/2003 | Thacker et al. | |
| 2003/0174066 | A1 | 9/2003 | Goetz et al. | |
| 2003/0199948 | A1 | 10/2003 | Kokones et al. | |
| 2003/0204161 | A1 | 10/2003 | Ferek-Petric | |
| 2003/0204221 | A1 | 10/2003 | Rodriguez et al. | |
| 2003/0204222 | A1 | 10/2003 | Leinders et al. | |
| 2003/0204223 | A1 | 10/2003 | Leinders et al. | |
| 2003/0204224 | A1 | 10/2003 | Torgerson et al. | |
| 2003/0212445 | A1 | 11/2003 | Weinberg | |
| 2003/0216666 | A1 | 11/2003 | Ericson et al. | |
| 2003/0236558 | A1 | 12/2003 | Whitehurst et al. | |
| 2004/0011137 | A1 | 1/2004 | Hnat et al. | |
| 2004/0015202 | A1 | 1/2004 | Chandler, III et al. | |
| 2004/0015204 | A1 | 1/2004 | Whitehurst et al. | |
| 2004/0015205 | A1 | 1/2004 | Whitehurst et al. | |
| 2004/0016298 | A1 | 1/2004 | Scott | |
| 2004/0019369 | A1 | 1/2004 | Duncan et al. | |
| 2004/0019382 | A1 | 1/2004 | Amirouche et al. | |
| 2004/0019384 | A1 | 1/2004 | Kirking et al. | |
| 2004/0073221 | A1* | 4/2004 | Biscup | 606/73 |
| 2004/0102820 | A1 | 5/2004 | Mouine et al. | |
| 2005/0222569 | A1* | 10/2005 | Panjabi | A61B 17/7028 606/257 |
| 2006/0036259 | A1* | 2/2006 | Carl | A61B 17/70 606/90 |
| 2006/0136061 | A1* | 6/2006 | Navarro | A61F 2/442 623/17.13 |

FOREIGN PATENT DOCUMENTS

| | | |
|---|---|---|
| DE | 3414992 | 10/1985 |
| DE | 3442549 | 5/1986 |
| DE | 4442930 | 6/1996 |
| DE | 10137011 | 2/2003 |
| EP | 0553517 | 8/1993 |
| EP | 0611583 | 8/1994 |
| EP | 0561068 | 3/1999 |
| EP | 0611583 | 4/1999 |
| EP | 1351428 | 10/2003 |
| EP | 0956811 | 12/2005 |
| EP | 1671577 | 6/2006 |
| EP | 1854503 | 11/2007 |
| FR | 2875972 | 3/2006 |
| GB | 2223406 | 4/1990 |
| JP | 5277195 | 10/1993 |
| JP | 9098978 | 4/1997 |
| JP | 2000237219 | 9/2000 |
| WO | 90/06720 | 6/1990 |
| WO | 95/32673 | 12/1995 |
| WO | 01/78226 | 10/2001 |
| WO | 2005/000090 | 1/2005 |
| WO | 2005/049105 | 6/2005 |
| WO | 2005/074821 | 8/2005 |
| WO | 2005/120203 | 2/2006 |
| WO | 2006/045607 | 5/2006 |
| WO | 2006/098759 | 9/2006 |

* cited by examiner

ORTHOPAEDIC IMPLANT WITH SENSORS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATION DATA

The present application is *a Reissue Application of the U.S. patent application Ser. No. 13/298,808 filed on Nov. 17, 2017, now U.S. Pat. No. 8,551,092; which is* a Continuation application of U.S. patent application Ser. No. 11/147,750 filed on Jun. 7, 2005, now U.S. Pat. No. 8,083,741, which claims priority to U.S. Provisional Patent Application Ser. No. 60/578,107, filed Jun. 7, 2004, the entire contents of which are expressly incorporated herein by reference thereto.

FIELD OF THE INVENTION

The present invention relates to orthopaedic implants, such as bone plates, for use in repairing fractured bones or for addressing other orthopedic conditions. More particularly, the present invention relates to an orthopaedic implant having sensors and/or a microchip for measuring and transmitting data concerning the implant and/or the surrounding tissue to doctors and/or patients.

BACKGROUND OF THE INVENTION

Bone plates have been used for many years in the field of orthopedics for the repair of broken bones and are well known in the art. One example of such a bone plate is shown and described in U.S. Pat. No. 6,623,486 to Weaver, et al. which is hereby incorporated by reference. Such bone plates function well in most instances, and fracture healing occurs more predictably than if no plate were used. In some instances, however, improper installation, implant failure, infection or other conditions such as patient non-compliance with prescribed post-operative treatment may contribute to compromised healing of the fracture, as well as increased risk to the health of the patient. Health care professionals currently use non-invasive methods such as x-rays to examine fracture healing progress and assess condition of implanted bone plates. However, x-rays may be inadequate for accurate diagnoses. They are costly, and repeated x-rays may be detrimental to the patient's and health care workers' health. In some cases, non-unions of fractures may go clinically undetected until implant failure. Moreover, x-rays may not be used to adequately diagnose soft tissue conditions or stress on the implant. In some instances, invasive procedures are required to diagnose implant failure or infections early enough that appropriate remedial measures may be implemented.

Therefore there is a need for an orthopaedic implant that can provide precise and accurate information to doctors and patients concerning the status of the implant, progress of fracture healing, and the surrounding tissue without the need for x-rays or invasive procedures.

SUMMARY OF THE INVENTION

The present invention comprises an orthopaedic implant, e.g., a bone plate, intramedullary nail, etc., for fixation of bone having one or more microchips (i.e., integrated circuits) and various sensors for the gathering of information relating to the implant and its environment.

An implant is provided comprising a body portion configured to contact patient tissue, one or more microchips, and a plurality of sensors arranged on the implant body and connected to said microchip wherein at least one sensor is configured to receive physical stimulus from a portion of the implant or the patient's tissue. The microchip may further comprise a data logger and a power source, such as a battery.

The implant may be a bone plate, bone screw, intramedullary nail, spinal fixation element (pedicle screw, pedicle hook, fixation plate, fixation rod, etc.), intervertebral implant (artificial spinal disc or fusion spacer), distractor, external fixation system or other orthopaedic implant. The implant may have a coating, which may include a polymer or a porous metal, and may act as a carrier or substrate for a pharmaceutically active agent or other therapeutic substance. The implant may also include a compartment for storing a therapeutic agent, such as an antibiotic, a growth factor, a chemotherapeutic agent, etc. The therapeutic agent may be released in response to a signal received by the microchip.

One or more sensors on the implant may be configured and adapted to receive a strain from at least a portion of the implant. The sensors may be configured and adapted to receive a pressure applied to at least a portion of the implant, and/or to receive a temperature of at least a portion of the implant. The sensors may also be configured to capture digital images (video and/or photographs) of the surrounding patient tissue. The sensors may also be configured and adapted to emit an electric current for stimulating bone growth.

The patient tissue may comprise first and second bone portions of a fracture, the implant may further comprise an element configured to apply a micro-motion to the first and second bone ends to facilitate fusion of the fractured portions.

The implant may further comprise a counter for counting a number of loading cycles applied to the implant.

In another embodiment, an implant for the fixation of bone comprises a plurality of holes for accepting fasteners, an onboard microchip comprising a data logger, signal conditioner, multiplexer, and transmitter, and a plurality of sensors connected to the microchip and arranged at various points on said implant, wherein said sensors are configured to receive at least one physical stimulus at a portion of the implant.

One of said sensors may be selected from at least one of the group consisting of a pressure transducer, a thermocouple, a strain gauge and a cycle counter.

In another embodiment, the present invention relates to a method of mending a broken hone, comprising providing a bone fixation implant with a microchip, arranging a plurality of sensors on said implant, connecting said plurality of sensors to said microchip, affixing the implant to first and second portions of the broken bone using a plurality of fasteners, providing data from said sensors to said microchip, and transmitting said data from said microchip to an external receiving device.

In another embodiment, a monitoring system is provided comprising an implant having at least one sensor and configured for at least partial insertion into a patient, a microchip associated with the implant and the sensor, the microchip configured to receive at least a first signal from the sensor, a transmitter associated with the microchip for transmitting a second signal, representative of the first signal, a receiver located outside of the patient, the receiver configured receive the transmitted second signal, and a display device associated with the receiver, the display device configured to provide an audible or visual representation of the second signal to a user. The display device may be further configured to continuously record the transmitted second signal.

The implant may be coated. Such a coating may include a polymer or porous metal, such as magnesium, that can be a carrier or substrate for a pharmaceutically active agent or synthetic agent.

BRIEF DESCRIPTION OF THE DRAWINGS

To facilitate an understanding of and for the purpose of illustrating the present invention, exemplary and preferred features and embodiments are disclosed in the accompanying drawings, it being understood, however, that the invention is not limited to the precise arrangements and instrumentalities shown, and wherein similar reference characters denote similar elements throughout the several views, and wherein.

DETAILED DESCRIPTION OF THE PREFERRED EMBODIMENT

Figure 1:
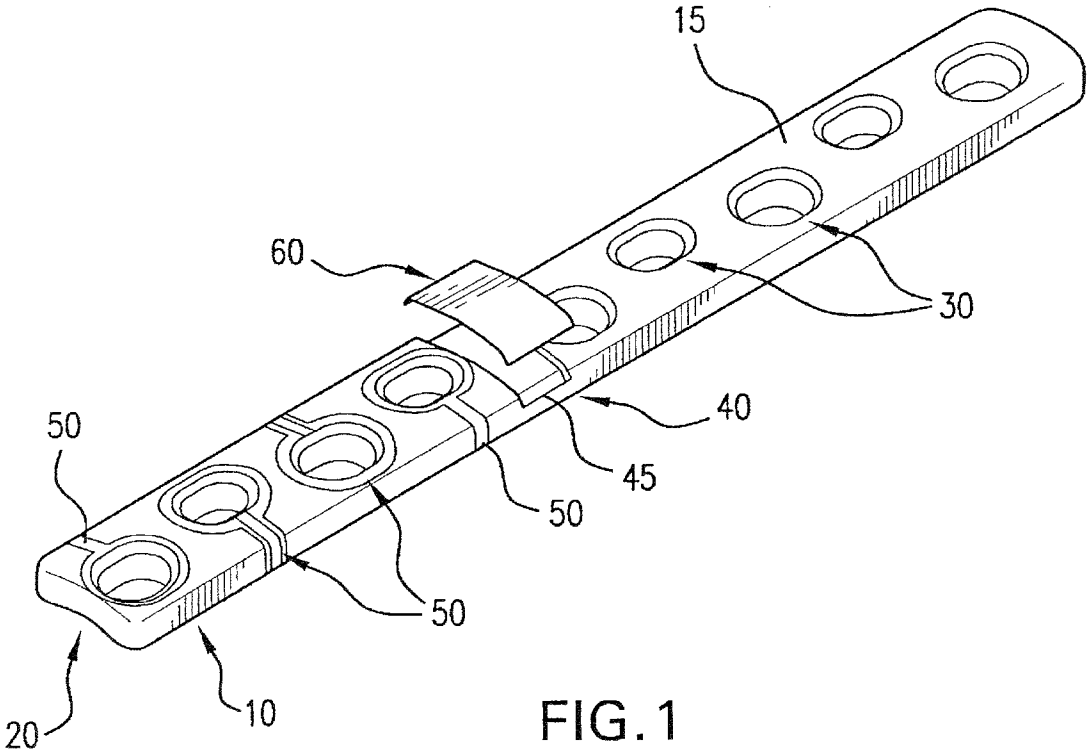
FIG. 1 is a perspective view of a first embodiment of a bone plate according to the present invention.
Figure 2:
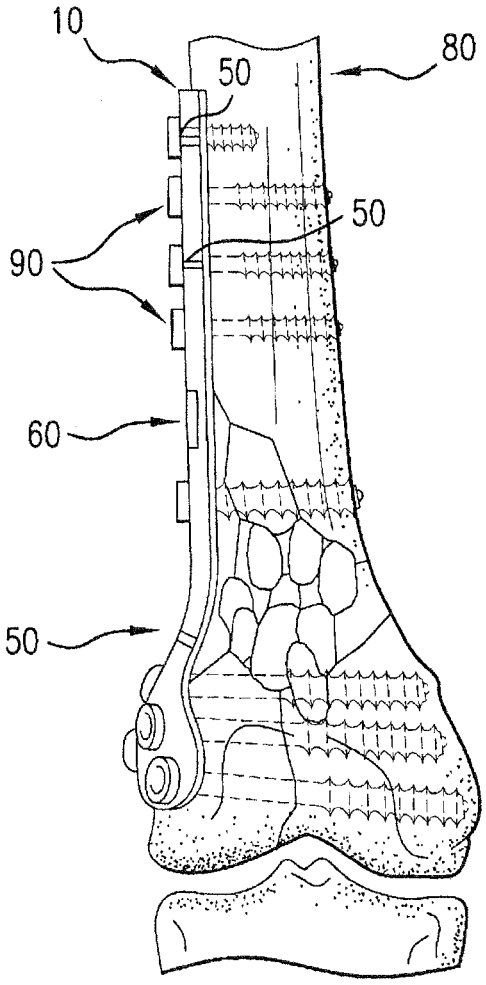
FIG. 2 is a side view of a second embodiment of a bone plate according to the present invention attached to a bone.

Reference is now made to FIGS. 1-2, which show a bone plate 10 according to a first preferred embodiment of the present invention. The bone plate 10 shown in FIG. 1 comprises upper surface 15 and lower surface 20, with the lower surface 20 configured to contact the bone. The plate may further have a number of holes 30 configured and adapted to receive fasteners, such as, for example, screws, that will affix the bone plate to the bone. One or more microchips 40 may be located on the plate top surface 15, bottom surface 20, the side wall of the bone plate, or as with the illustrated embodiment, may be placed within a compartment 45 in the bone plate for recording information gathered by numerous sensors 50 which may be located at various locations anywhere on the top, bottom or sides of the plate, or may surround or be located within the plate holes. The sensors may be located on the surface of the plate, or they may be embedded therein. A small cover 60 may be provided to conceal and protect microchip 40 within the bone plate. The cover 60 may seal the microchip from exposure to the environment within which the bone plate is placed. Alternatively, microchip 40 may not be covered and may be openly exposed. While reference is made to a plate having the configuration illustrated in FIG. 1, it will be noted that one or more microchips 40 and sensors 50 may be used in conjunction with any appropriate fixation device known in the art, e.g., intramedullary nails, screws for external or internal fixation, spinal fixation elements (pedicle screws, hooks, fixation rods, etc.), intervertebral implants (artificial spinal disks and spacers), distractors for lengthening bones and correcting deformities, etc. Furthermore, it should be emphasized that multiple microchips 40 and/or multiple sensors 50 may be provided for a single fixation device to monitor different segments of the fixation device or to monitor different types of sensors (e.g. strain, pressure, temperature, cycle count) provided with the plate. Moreover, microchips 40 located in one implant 10 can send and receive data to and from other implants. For example, a bone plate 10 located at one fracture site can send data to another plate 10 located at a different fracture site in the same or a different bone. Similarly, pedicle screws at one location can receive data from other pedicle screws, hooks or fixation rods. The implants of the present invention may also be used at an impending pathological fracture site, where information concerning increasing strain on the implant would indicate that the affected bone is weakening.

Similarly, such implants could also be employed at locations where osteotomies or resections have been performed to monitor bone strength.

In addition, the holes 30 in the bone plate 10 may be threaded to receive screws with threaded heads, as described in U.S. Pat. No. 5,709,686 to Talos, which is hereby incorporated by reference. The threaded connection between the screw and the plate may serve to lock the screw and plate together so that the screw will not back out of the plate even if the screw shank loses purchase with the surrounding bone, which can occur in patients having substandard bone structure resulting from osteoporosis or other factors. Standard compression screws having no such plate-locking feature may tend to pull out of substandard bone when subjected to the bending forces generated in the plate during post-installation loading. Further, standard compression screws are designed to engage the screw holes of the plate in a manner that forces the fractured bone ends together to aid healing. Thus, where a plate having only compression screws is installed across a fracture site, the bone portions may move slightly in the period following fixation. As a result, the measured strain in the plate during that period may not be truly representative of the true load-bearing capacity of the bone (i.e. it may be unnaturally high). Thus, a strain reading from a sensor on a plate using only compression screws may not provide the surgeon with reliable information regarding early healing of the bone (i.e. in the days or first week following implantation) from which he or she may make a diagnosis regarding whether the fracture is healing properly. Only after the fractured bone portions have settled will strain readings become sufficiently accurate that a proper diagnosis may be made. By contrast, where locking screws (i.e. those having heads that threadably engage the plate holes) are used, there is no period of settling, and thus the strain values observed in the plate will immediately upon implantation be representative of the load carried by the plate (and correspondingly the load carried by the bone). As such, the surgeon may use these early measured strain readings to develop an accurate, early assessment of the fracture healing rate and the potential for not uniting. An early diagnosis of delayed union is advantageous because it allows the surgeon to take remedial steps as soon as a possible non-union is suspected, thus prompting intervention.

FIG. 2 shows an alternate embodiment of the invention installed on a bone. FIG. 2 shows a bone plate 10 attached to a bone 80 by several screws 90. Bone plate 10 may have curved, flared, or bent sections. The microchip cover 60 protects and covers one or more microchips 40. The various sensors 50 that wrap around different parts of the bone plate can also be seen.

Figure 3:
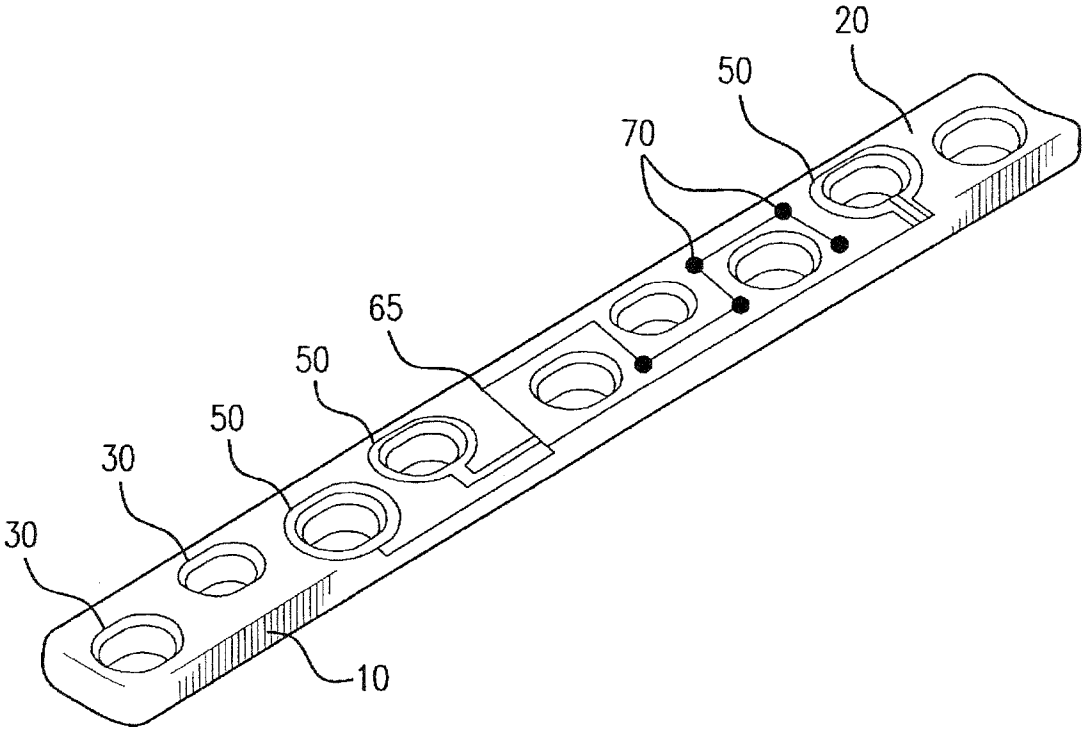
FIG. 3 is a perspective view of the underside of an embodiment of a bone plate according to the present invention.

FIG. 3 shows the underside of an embodiment of the bone plate 10, showing holes 30 and sensors 50. On the surface of the bone plate that attaches to the bone there may also be one or more electrodes 70 for the stimulation of bone growth. There may also be a small opening 65 for the various sensor electrodes to enter the bone plate and connect with the microchip contained therein. Opening 65 may also hold a pharmaceutically active agent, such as a bolus of antibiotics, chemotherapy agents, pain medication and/or other therapeutic agents. The agent may be released by the implant in response to a signal conveyed by the treating physician or the patient, or may be dispensed automatically by the implant when an elevated temperature or other data signaling a need for the agent is recorded by one or more of sensors 50. In one embodiment, the agent may include growth factors, such as Bone Morphogenetic Proteins (BMPs) or Vascular Endothelial Growth Factor (VEGFs). In other pathologic applications, the agent may include angiogenesis inhibitors, e.g., fibulin-5, which act to deprive tumors of nutrients and oxygen. In other reconstructive applications, the pharmaceutically active agent may include drugs with the ability to stimulate hair growth in areas of the scalp, such as Minoxidil®. Sensors 50 may comprise pressure sensors disposed along the underside of the plate, and may be used to measure compression of the plate to the underlying bone (further described in relation to FIG. 5 below). 1

Figure 4:
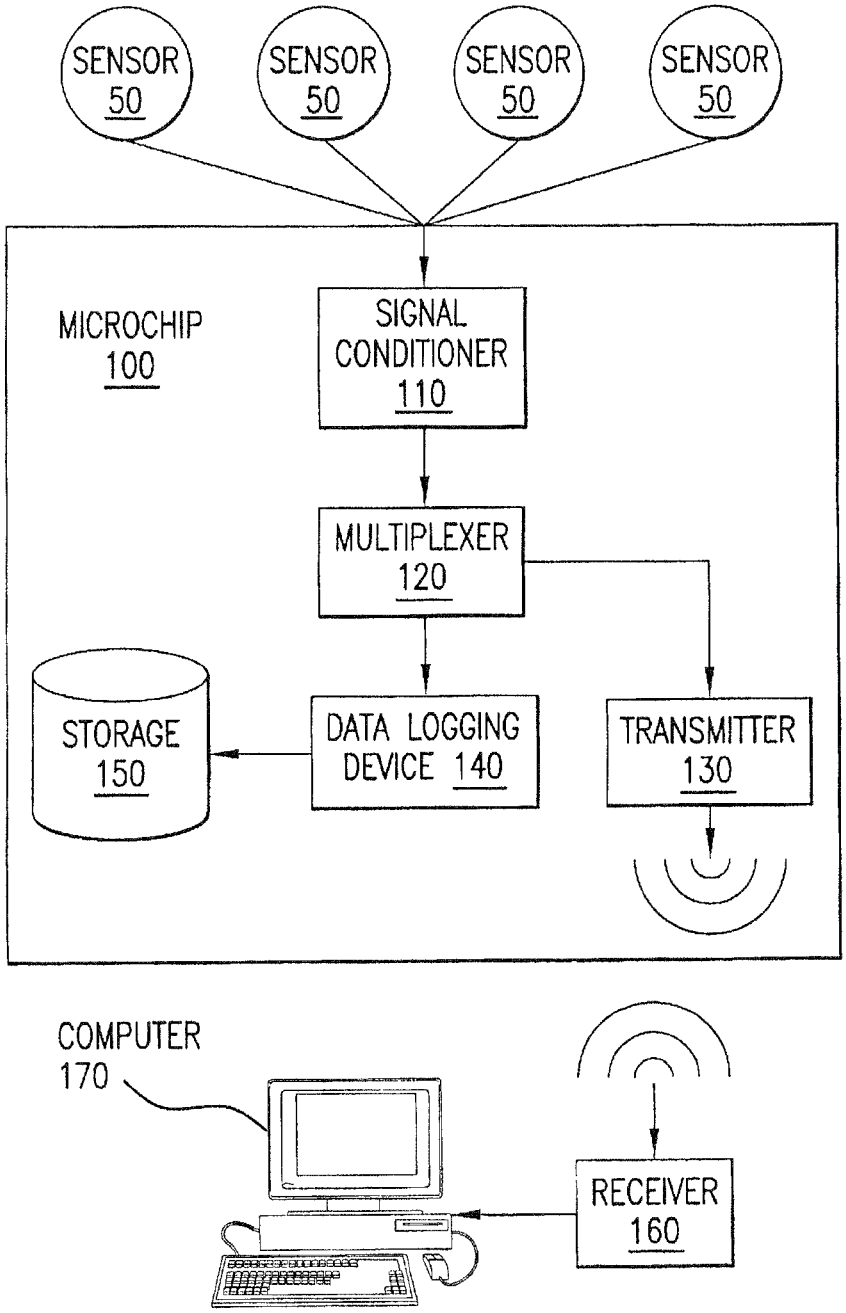
FIG. 4 is a block diagram of an embodiment of the various microchip components.

As seen in FIG. 4, the implant may contain a microchip 100 which may include a data logger 140, signal conditioner 110, multiplexer 120, and transmitter 130. The microchip may be connected to one or more sensors 50 attached at different locations along the implant. The sensors may be used to monitor loading of the implant by measuring strain at the individual locations and count the cycles of loading and unloading. Alternatively, the sensors may be configured to measure conditions immediately surrounding the implants; such as temperature, pH, etc. Sensors 50 and/or microchip 40 may also include digital photographic capabilities, such as a CMOS chip, which can capture and transmit images or video of patient tissue in the vicinity of the implant.

Figure 5:
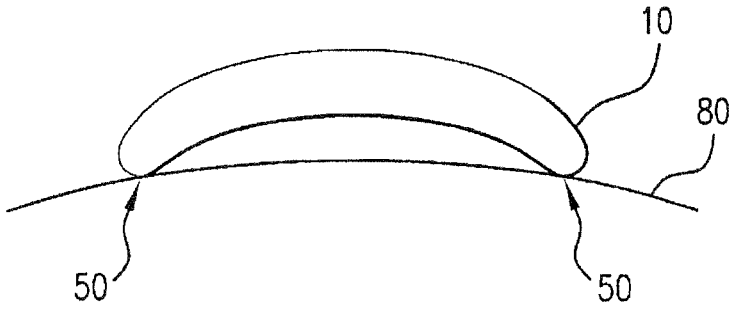
FIG. 5 is a cross-section of a bone plate according to the present invention as attached to a bone.

FIG. 5 is a cross-section of one embodiment of a bone plate 10 according to the present invention as attached to the bone 80. This figure shows how the bone plate 10 is semi-curved but has a different curvature from the bone 80 so that the bone plate only contacts the bone along the edges, or rails, of the bone plate. This type of contact is useful in minimizing the disruption of blood flow to the bone as described in U.S. Pat. No. 6,309,393 to Tepic, which is hereby incorporated by reference. Thus, sensors 50 disposed between the edges or rails of the plate and the bone surface may detect the compression force between the bone and the plate at those sensor locations. Resulting initial force measurements may be used to provide a baseline for the engagement of the plate with the bone immediately following implantation. Subsequent measurements may then he compared to the baseline measurements to determine whether the plate remains sufficiently engaged with the bone, or whether remedial action is required (e.g. the plate or screw (s) need to be replaced). The ideal fixation case is one in which the compression force between plate and bone remains constant from the time the implant is installed to the time it is removed. Where multiple individual sensors are disposed along the plate rails, subsequent readings associated with each sensor can be used to individually identify the condition of each screw in the plate, and may also be used to assess the overall integrity of the connection between the bone and the plate.

Thus, the various sensors arranged on the implant may include thermocouples, pressure transducers, force probes, counters, strain gauges, and digital imaging devices. At least one sensor may be used to count the number of loading cycles the implant experiences, including axial, bending and torsional loads. The information gathered from these sensors may be used to diagnose conditions associated with the implant and/or the tissue surrounding the implant.

For example, it may be important to monitor strain at various locations on the implant, since such strain may be directly related to forces applied to and experienced by the implant. Monitoring the force applied to the implant, e.g., a bone plate, over time may allow the doctor to determine whether the bone is healing at the appropriate rate. As a bone heals, the amount of load carried by the bone will increase, and a proportionally lower load will be carried by the implant, and thus a lower strain will be measured by a strain gauge mounted to the plate. If the measured plate loading does not decrease at the expected rate, the doctor may take remedial action. Similarly, early detection of an overloading condition in the plate may allow the doctor to correct or replace an over-stressed or fatigued plate or fastener. It has been observed that non-unions are clinically diagnosed six months after the fracture event. If the strain gauge does not detect transfer of loading conditions, it may indicate delayed union and could signal potential damage to the implant or the end of its useful life.

One or more sensors may also be used to monitor the number of loading cycles, e.g., axial, bending, torsional, etc., experienced by the implant. One cycle may be defined as an application of stress to the implant followed by the release of that stress. For example, if the implant is installed along the femur of a patient, one cycle could be one step in which the patient puts pressure on the implant as his or her foot hits the ground followed by a release of that stress when the patient lifts his or her foot from the ground. The life of an implant is usually determined by how many cycles it experiences until bone healing occurs or until the implant fails. A doctor can determine when an implant needs to be replaced by using a counter programmed to log the amount of cycles the implant has been through. In addition, such a counter may be useful in determining the cause of an implant failure, such as due to over-activity of the patient or clinical non-union of the fracture.

It may also be desirable to obtain temperature readings at various locations along the implant to determine whether the tissue surrounding the implant is infected following implantation. Normal healthy human tissue has a temperature in the range of from about 36 degrees Celsius to about 37.5 degrees C. It has been observed that infected tissue may evidence an increase in temperature to a range above about 38 degrees C. Thus, if such a temperature increase is detected by one or more of the temperature sensors on the implant, the doctor may choose to initiate a regimen of antibiotics, or may take other more invasive actions to eliminate the infection. In one embodiment, as discussed above, the treating physician may send a signal to the implant to release a bolus of antibiotics stored in a compartment within the implant in order to treat an infection, or, alternatively, the implant itself may be configured to automatically release antibiotics if a certain threshold temperature is reached. Abnormally high tissue temperatures in the vicinity of the implant may also signal that the patient is experiencing an adverse reaction to the material of the implant. For example, if the implant is made of or contains a material to which the patient is allergic (e.g. nickel), the patient's body may react to the implant in a manner similar to that of an infection. Thus, patient rejection of the implant may likewise be determined through temperature measurement. Digital photographic elements within sensors 50 in the implant may also be used to view images of patient tissue for signs of infection and/or implant rejection.

Since body temperatures may be influenced by factors such as exercise, temperature readings would likely take place in the doctor's office or other controlled setting, rather than being constantly monitored or monitored by the patient. The temperature sensors preferably will be located anywhere on the surface of the plate, except between the plate and the bone. Monitoring of temperatures through sensors mounted on a bone plate thus may aid the doctor in making an important early diagnosis of infection, increasing the chance that the infection may be effectively contained. In still other embodiments, sensors 50 on implant 10 may detect chemical agents/reagents formed by and in the patient's surrounding tissues.

Reference is now made to FIG. 4 which is a block diagram of a microchip contained on the implant of the present invention. In one embodiment, the microchip 100 may contain a data logging device 140 for storing information recorded by the sensors. The microchip may also contain a signal conditioner 110 for powering the sensor and preparing the signal received by the sensor, a mutiplexer 120 for combining information received from numerous sensors, and a transmitter 130 or transmitting the information received from the sensor or sensors. As information is received by one or more sensors 50, it is passed through the signal conditioner 110 to the multiplexer 120 and on to both the data logging device 140 which may store information in storage 150 provided on microchip 100 and the wireless transmitter 130 which transmits the information to a receiving device 160 which may be connected to a computer 170. Device 160 can both send data to and receive data from microchip 100. In addition, in an alternate embodiment, wireless transmitter 130 may be replaced with a hard wired connection.

In one embodiment the receiving device is a wireless hand-held computer, such as a Pocket PC®, Palm Pilot®, Blackberry® device or cellular telephone, that may be used to request information from the implant, store information sent by the implant, and send information to the implant. For example, the surgeon may pass the handheld device over the portion of the patient's body containing the implant, and the device may upload strain, temperature, pH, and/or pressure data from one or more sensors located on the implant. Thereafter, software associated with the microchip 100, sensors 50 and/or handheld device 160 may manipulate the uploaded data to provide a visual readout to the surgeon. Such a readout may comprise discrete force, temperature and pressure and stress cycle values taken from the individual sensors. The readout may also comprise a graph of the values obtained from the same patient over time. It may also provide an alarm feature that would signal a dangerous condition such as substantial implant overloading, substantial loss of compression between implant and bone, a high temperature condition indicative of infection, and/or an abnormally low or high cyclic loading count indicating the patient is either not participating in the proscribed recuperative therapy or is exerting him or herself more than a prescribed amount. In one embodiment, the software may display an image of the particular implant with measured force, pressure and temperature readings displayed at or near the actual location of the sensors on the implant. Further, instead of a discrete numerical readout associated with each sensor, the image may simply be color-coded to indicate satisfactory or unsatisfactory (i.e. alarm) conditions. Thus, in an exemplary embodiment, portions of the plate that are experiencing expected values of strain, pressure, pH, time, cycle count and temperature would appear in blue, whereas portions of the plate experiencing much higher than expected values would appear in red. Threshold normal and high strain, temperature, pressure and cycle values may be programmed into the microchip on the implant, or may be selected by the surgeon using the handheld device or from another computer associated with the implant. The surgeon may then use a stylus to select desired portions of the implant on the screen, and specific loading, pressure, cycle count, time, and/or temperature data would be displayed for the affected (i.e. red) area of the implant. In other embodiments, the receiving device may include external diagnostic equipment such as a CT scanner, which can send and receive data to and from the implants 10, and/or other handheld devices 160. The method of communication between implants 10 and/or devices 160 may include infrared communication.

In one embodiment, the microchip 100 and data logging device 140 may contain implant-specific information supplied by the manufacturer such as implant type, sensor type, implant/sensor manufacturing date, location, lot, etc. Calibration data for each sensor may also be contained therein. Further, the microchip 100 and data logging device 140 may contain all of the historical readings from all of the sensors associated with the implant. The microchip 100 may also be programmed to perform manipulation of the data received from the sensors. Thus, in one embodiment the handheld device may perform minimal manipulation of data and may instead simply display data that has already been manipulated by the microchip 100 and stored by the data logging device 140. Alternatively, the handheld device may be used to perform some data manipulation.

Thereafter, the doctor may transmit the information from the handheld device to a desktop computer or web server for long term storage or for further manipulation as desired. In one embodiment, data may be transmitted anonymously to the manufacturer confidentially via the internet or other secure transmission method (to protect patient privacy). The manufacturer may then use such data to assist in designing future implants. The implants 10 and sending/receiving device 160 may also be configured for satellite communication.

In one embodiment, the microchip may be programmed to turn on and off at predetermined intervals in order to transmit information only at certain times of the day. Such an arrangement may be advantageous where the microchip is powered by a battery, and may thus may act to conserve battery power. Alternately, the microchip may be configured to continuously transmit data throughout the life of the implant. This may be useful when a computer is used to continuously gather the information so that graphs may be made of different variables, such as temperature, strain, load and fatigue, and how these variables may change throughout the day, including how the patient's activities may affect the variables and whether and how such variables may affect the implant.

As earlier noted, the information stored in the data logging device 140 may be sent to a receiver 160 outside the body using a wireless (i.e., radio frequency (RF), infrared, etc.) transmitter 130. The wireless receiver may be connected to a handheld device or a personal computer 170 so that the patient and/or surgeon may view information transmitted from the bone plate or may send the information over the Internet to a recipient for analysis. In an alternative embodiment, data stored by implant 10 may be transmitted to a receiver 160 outside the body using a hard wired connection.

Alternately, the patient in whom the implant is installed may have a receiver in their home or office. The microchip may be configured to transmit a signal wirelessly to the receiver station if a certain condition occurs. For example, if the microchip senses an increase in temperature over a predetermined temperature, it may send an alarm signal to the base station, which may then issue an alarm signal audible to the user. Similar alarms based on over-strain, under-pressure, or over-cycling conditions may likewise be implemented. Alarm signals received by a wireless base station may also be sent automatically by the base station over the Internet to a doctor who may contact the patient with immediate instructions.

In one embodiment, the microchip may be powered using the principle of induction. In this embodiment, one coil of wire is attached to the microchip within the implant and one coil of wire is embedded in a reader device located outside the patient. Excitation in the coil located outside the patient will produce an excitation in the coil within the implant. A remote energy source, such as an ultrasound device, may be used to excite the induction coils. This arrangement may operate like a transformer to power the microchip, thus obviating the need for battery power.

In an alternate embodiment, the implant may use a piezoelectric crystal which will use the loading and unloading cycle of the bone plate to generate a voltage which may be used to power the bone plate.

In yet another alternate embodiment, the microchip may use piezoelectric technology to create micro-motion within the implant. This micro-motion may be transmitted to the bone to facilitate healing of the bone. Alternatively, the micro-motion inherent in a healing bone may be used to power the microchip. Thus, a piezoelectric crystal may be used to receive the micro-motion and convert the motion to a charge that may power the device.

Referring again to FIG. 2, a specific positioning of the sensors on bone plate 10 is illustrated. In this embodiment, the sensors 50 are positioned around the screw holes to provide information to the doctor or patient concerning the location of the screws and the stress placed on the bone plate by each screw. However, one skilled in the art would recognize that sensors of such small size may be located on any part of the bone plate and thus may be used to provide information regarding physical characteristics of the bone plate sections and/or the environment associated with individual bone plate sections.

In another embodiment, the microchip may be used to send electric current through electrodes 70 located on different locations of the bone plate in order to electronically stimulate growth of the bone. Such stimulation may speed bone growth and recovery, and such phenomenon are well known in the art. One example of electrical current used to stimulate bone growth in implants and increase infection resistance of any antibacterial agents used with the bone plate is described in U.S. Pat. No. 6,663,634 to Ahrens et al., which is hereby incorporated by reference.

In a further embodiment, at least a portion of the bone plate may be coated, where the coating may include a polymer or porous metal, such as magnesium, that can act as a carrier or a substrate for a pharmaceutically active agent or synthetic agent. Such agents can include antibiotics, microbicides, growth factors (BMPs and/or VEGFs), angiogenesis inhibitors (fibulin-5) or chemotherapeutic agents. The coating may be biodegradable in the patient. A non-limiting exemplary coating is described in detail in U.S. patent application Ser. No. 09/801,752 to Schmidmaier et al., filed on Mar. 9, 2001, which is hereby incorporated by reference.

In one embodiment, the microchip may transmit information wirelessly by radio frequency (RF) as known in the art. The bone plate may also be encoded with information such as when the plate was installed and who installed it so that doctors can access this information from the plate by using radio frequency identification (RFID).

Figure 7:
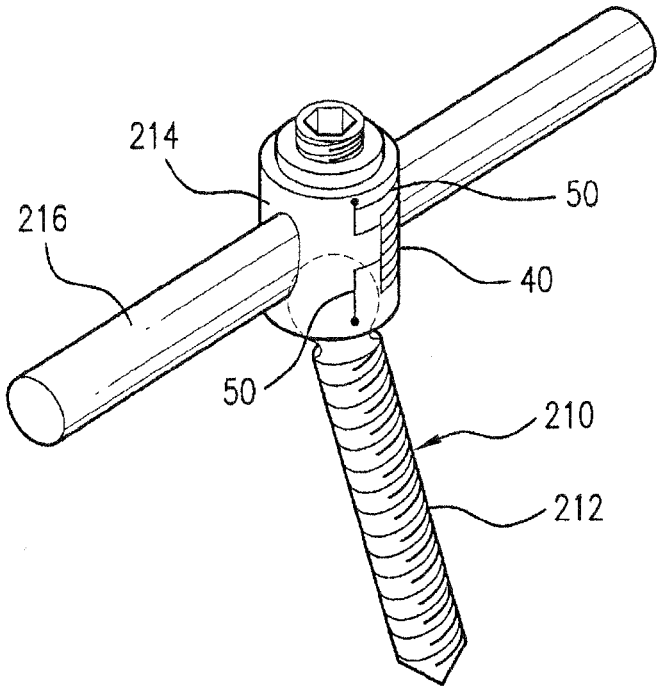
FIG. 7 is a perspective view of a pedicle screw according to another preferred embodiment of the present invention.

Although the present invention has been shown and described in connection with an implanted bone plate, one skilled in the art would recognize that the present invention can also be practiced with other types of orthopaedic implants, such as bone screws, intramedullary rods, spinal fixation elements and implants (e.g., pedicle screws, hooks, etc.), external fixators and distractors. One example of such a bone screw is shown and described in U.S. Pat. No. 6,306,140 to Siddiqui which is hereby incorporated by reference. Siddiqui describes a bone screw inserted into bone which is suitable for stabilizing a fractured bone. The bone screw has threads and provides compression to stabilize different regions of bone. A microchip may be installed within the bone screw with one or more sensors located at different locations on the bone screw to monitor stress, strain, temperature and pressure. FIG. 7 shows a pedicle screw 210, having threads 212 and an upper portion 214 for connection to a fixation rod 216. Pedicle screw 210 includes one or more microchips 40 and sensors 50. which function as described above with reference to implant 10.

An embodiment of a bone pin which may be used in connection with the present invention is shown and described in U.S. Pat. No. 6,663,634 to Ahrens et al. Ahrens discloses a bone pin for insertion into bone that is coated with an antibacterial agent. The bone pin as disclosed in Ahrens may be adapted to practice the present invention by installing a microchip within the bone pin and one or more sensors located on the bone pin.

Figure 6:
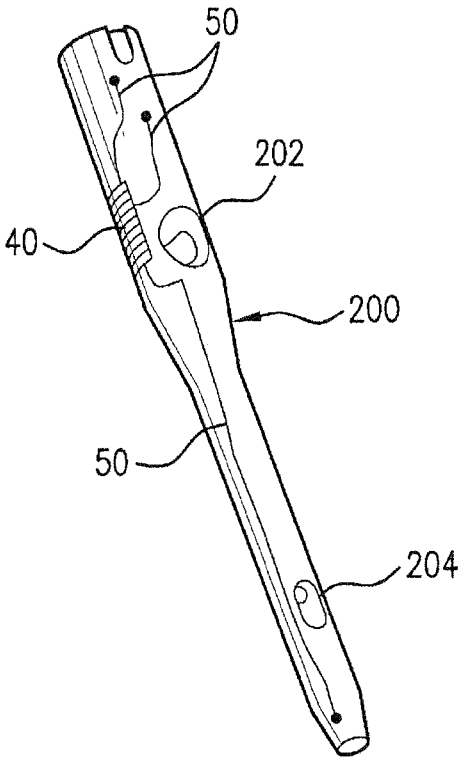
FIG. 6 is perspective view of an intramedullary nail according to a preferred embodiment of the present invention.

As shown in FIG. 6, the present invention may also be practiced in a similar manner in connection with an intramedullary nail 200 having one or more openings 202, 204 for receiving locking elements and/or cross members. Intramedullary nail includes one or more microchips 40 and sensors 50 for collecting and transmitting data concerning the implant and/or the surrounding patient tissue. A cross-member (not shown) used with an intramedullary nail 200, which may pass through an upper opening 202 and penetrate the femoral head when repairing femoral fractures, may also include one or more microchips 40 and sensors 50. Another example of an intramedullary nail is shown and described in U.S. Pat. No. 6,607,531 to Frigg which is hereby incorporated by reference.

Figure 8:
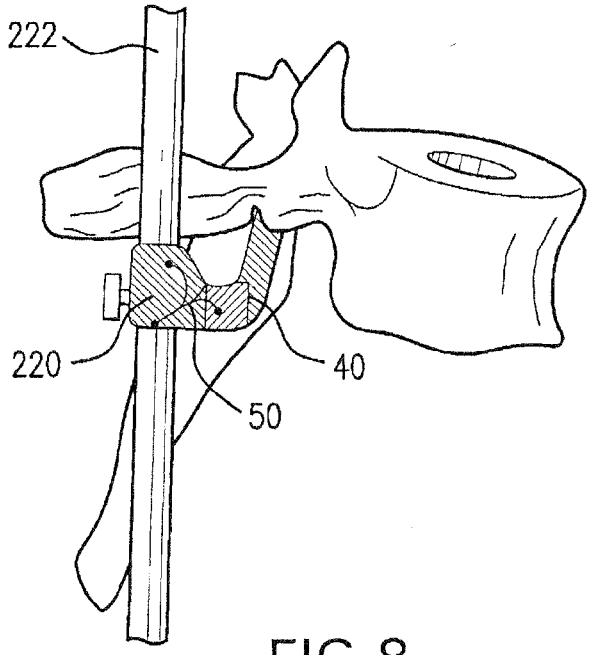
FIG. 8 is a perspective view of a pedicle hook according to yet another preferred embodiment of the present invention.

As discussed above, the present invention may also be practiced in connection with spinal fixation devices such as pedicle screws 210 (FIG. 7), pedicle hooks 220 (FIG. 8), and fixation rods 216, 222 (FIGS. 7 & 8) for insertion into and/or attachment to the spinal column. In accordance with the present invention, the pedicle screw 210, pedicle hook 220 and/or fixation rod 216, 222 may contain one or more microchips 40 and one or more sensors 50 for the collection and transmission of strain, temperature, pressure and cycle data as previously described. Other pedicle screws and spinal fixation devices are shown and described in U.S. Pat. No. 6,325,802 to Frigg and U.S. Pat. No. 6,610,063 to Kumar et al., both of which are hereby incorporated by reference.

Figure 9:
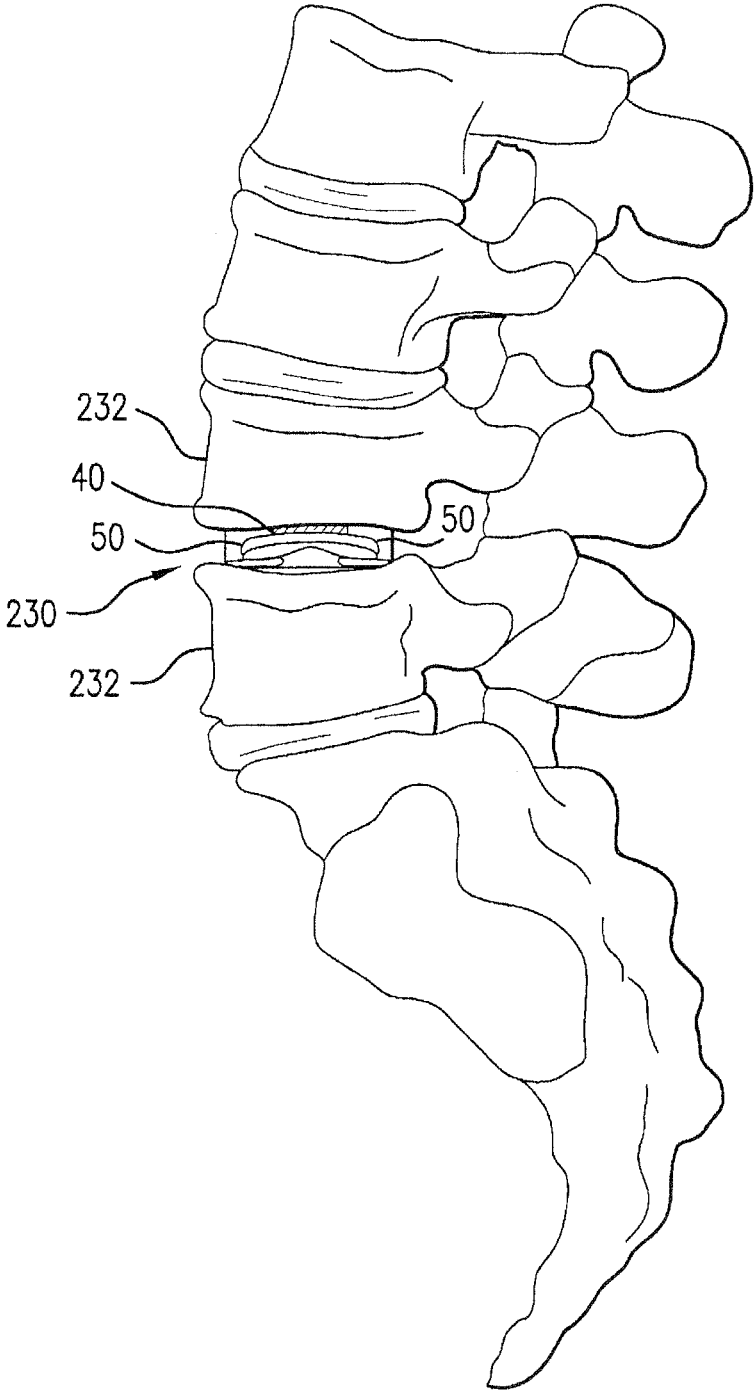
FIG. 9 is a side view of an intervertebral implant according to still another preferred embodiment of the present invention.

The present invention may also be practiced in connection with intervertebral implants, such as artificial spinal discs or spacers used in both fusion and non-fusion procedures for replacing damaged spinal discs. FIG. 9 shows an artificial spinal disc 230 inserted between two adjacent vertebrae 232 in the spinal column. Artificial disc 230 includes one or more microchips 40 and sensors 50, which function in the manner described above to collect and transmit implant/patient information.

Figure 10:
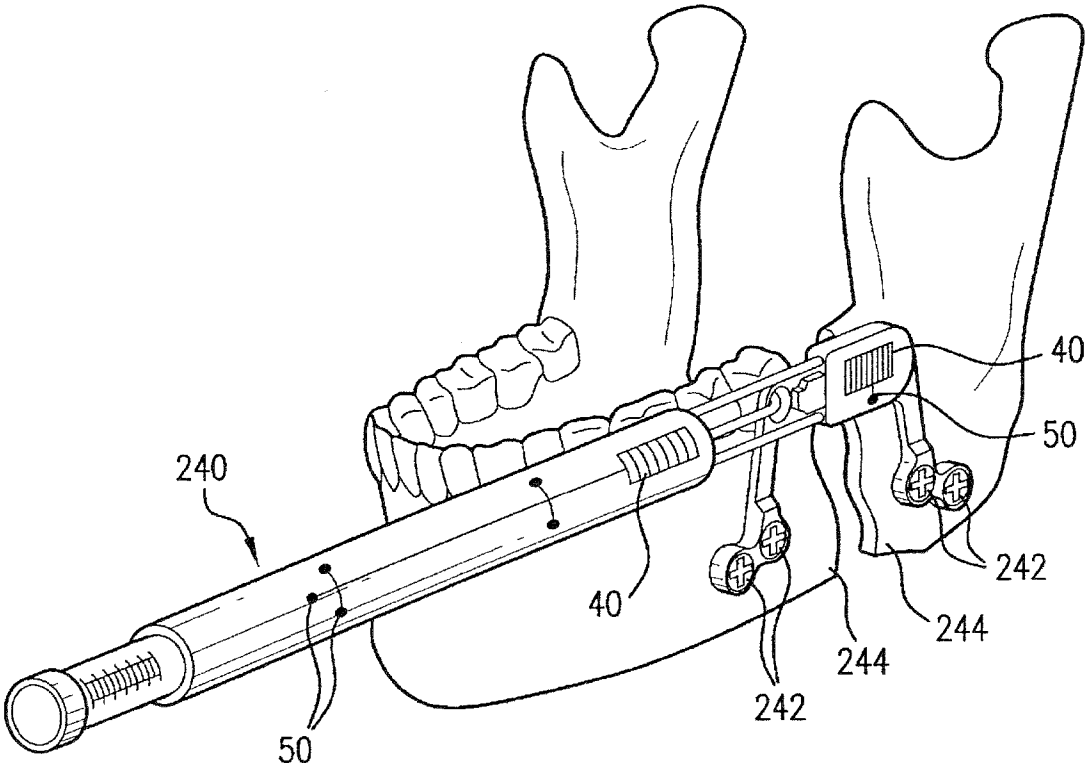
FIG. 10 is a perspective view of a maxillofacial distractor according to a preferred embodiment of the present invention.

As shown in FIG. 10, another embodiment of the present invention may be a distractor, such as a maxillofacial distractor. Distractor 240 is secured to bone segments 244 using bone screws 242, and includes one or more microchips 40 and sensors 50. In this embodiment, distractor 240 can provide live feedback to the physician or patient during adjustment of the distractor. In addition, microchip 40 may also be used to automatically drive the adjustment of the distractor (e.g., via motor, solenoid, etc.) based on the data recorded by microchip 40 and sensors 50 on distractor 240.

Figure 11:
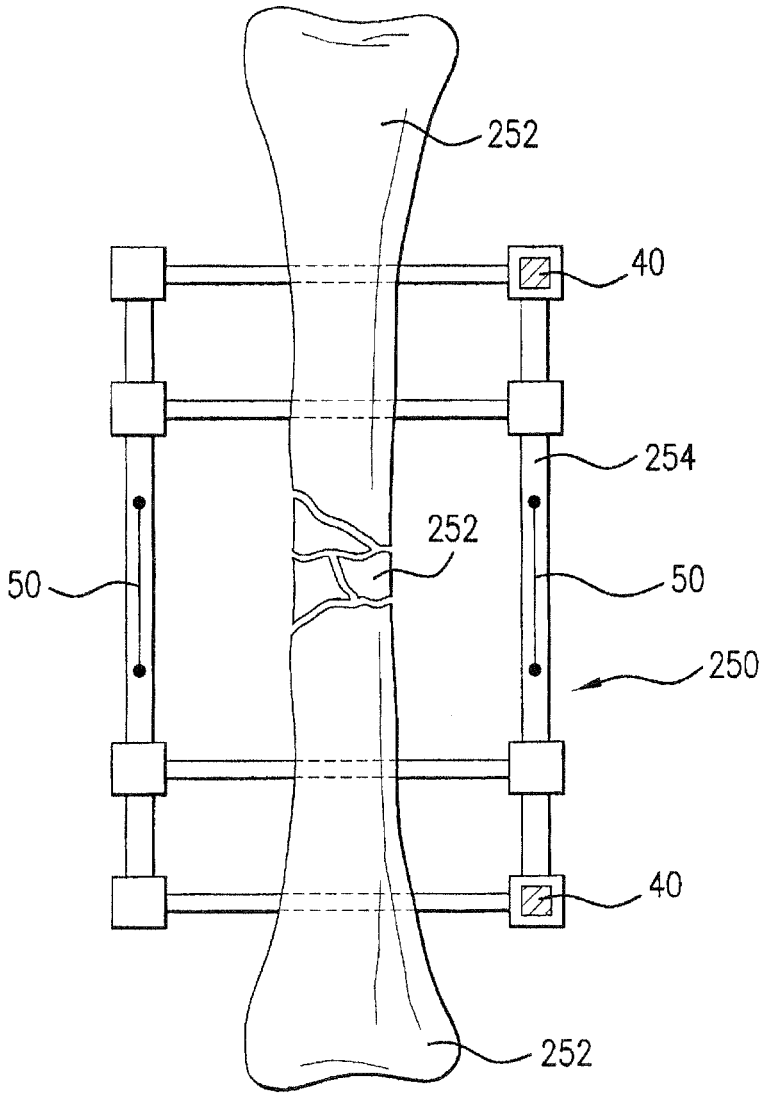
FIG. 11 is a side view of an external bone fixation system according to a preferred embodiment of the present invention.

Similarly, as shown in FIG. 11, the present invention may take the form of an external fixation apparatus, e.g., spatial ring, wrist fixator, or other bone fixation system. External fixator 250 is attached to bone segments 252 using rods 254. One or more microchips 40 and sensors 50 can record and transmit data concerning the fixation system to physicians and patients. As with distractor 240 discussed above, external fixator 250 can provide live feedback to the physician or patient during adjustment of the apparatus and microchip 40 may be used to automatically drive the adjustment of the fixator based on the implant and patient data recorded.

Another embodiment of the invention would provide for a centralized web server maintained by the manufacturer of the implants. The web server would be in communication with the various doctors that install and service the implants. When a doctor uses a computer or wireless device to collect information from the implant, the doctor may then transmit this information to the centralized web server. The manufacturer may then use this information to determine the average useful life of the particular implant model, and may also compile the data to determine what the common causes of failure for the implant model. The manufacturer also may also use this data to determine whether trends in implant success or failure may be used to educate surgeons on the most effective installation technique for a particular implant. This information may assist the manufacturer in designing new and improved implants, and in refining installation techniques.

While the present invention has been described with reference to the preferred embodiments, those skilled in the art will recognize that numerous variations and modifications will be made without departing from the scope of the present invention. This is especially true with regard to the specific shape and configuration of the implant and sensors. For example, sensors for measuring strain, temperature, compression and/or load cycling may be used in virtually any known orthopedic fixation application. Non-limiting examples of such applications are: plates used in maxillofacial fixation applications, footplates used with facial distraction systems, cranial flap clamps, pins used with external fixation devices, spinal fusion plates, spinal fusion rod assemblies, etc.

Accordingly, it should be clearly understood that the embodiments of the invention described above are not intended as limitations on the scope of the invention, which is defined only by the following claims.

What is claimed is:

1. A method of mending a broken bone, comprising:

affixing a bone fixation implant to first and second portions of the broken bone using a plurality of fasteners, the implant including a microchip and a plurality of sensors arranged on the implant and connected to the microchip, a first one of the sensors being in contact with a perimeter of a hole in a body portion of the implant for accepting a fastener;

collecting data from the sensors by the microchip; and transmitting the data from the microchip to an external receiving device.

2. The method of claim 1, wherein at least one of the sensors is a thermocouple.

3. The method of claim 1, wherein at least one of the sensors is a pressure transducer.

4. The method of claim 1, wherein at least one of the sensors is a strain gauge.

5. The method of claim 1, wherein at least one of the sensors is a digital imaging element.

6. A monitoring system comprising:

an implant having at least one sensor and configured for at least partial insertion into a patient, a first one of sensors being in contact with a perimeter of a hole in a body portion of the implant for accepting a fastener;

a microchip associated with the implant and the sensor, the microchip configured to receive at least a first signal from the sensor;

a transmitter associated with the microchip for transmitting a second signal, representative of the first signal;

a receiver located outside of the patient, the receiver configured receive the transmitted second signal; and a display device associated with the receiver, the display device configured to provide an audible or visual representation of the second signal to a user.

7. The monitoring system of claim 6, wherein the microchip further comprises a data logger.

8. The monitoring system of claim 6, wherein the display device is further configured to continuously record the transmitted second signal.

9. The monitoring system of claim 6, wherein the implant is a bone plate.

10. The monitoring system of claim 6, wherein the at least one sensor is configured and adapted to receive a strain from at least a portion of the implant.

11. The monitoring system of claim 6 wherein the at least one sensor is configured and adapted to receive a pressure applied to at least a portion of the implant.

12. The monitoring system of claim 6 wherein the at least one sensor is configured and adapted to receive a temperature of at least a portion of the implant.

13. The monitoring system of claim 6, wherein the implant further comprises a compartment for holding a therapeutic agent for release in response to a signal received by the microchip.

*14. The method of claim 1, wherein the bone fixation implant is a bone plate.*

*15. A method of orthopaedic surgery, comprising:*

*attaching an orthopaedic device to a bone using a plurality of fasteners, the orthopedic device including a microchip and a plurality of sensors operably connected to the orthopaedic device to monitor the orthopaedic device, the plurality of sensors being connected to the microchip,*

*intraoperatively adjusting the orthopaedic device, and*

*intraoperatively receiving data from the sensors via the microchip, the data corresponding to an adjustment of the orthopaedic device to achieve a desired spatial relationship of bone segments to one another.*

*16. The method of orthopaedic surgery of claim 15, further comprising the step of:*

*intraoperatively adjusting the orthopaedic device based on the data from the sensors.*

*17. The method of orthopaedic surgery of claim 15, wherein the bone segments are vertebrae and the orthopaedic device is a spinal fixation implant comprising a spinal fusion rod assembly.*

*18. The method of orthopaedic surgery of claim 15, wherein the data is wirelessly transmitted to an external computing device.*

*19. A method of orthopaedic surgery, comprising:*

*attaching a first rod of an orthopaedic device along a first side of a first portion of a bone via a first transverse member extending from the first rod, the first rod having a first sensor operably connected thereto;*

*attaching a second rod of the orthopaedic device along a second side of a second portion of the bone via a second transverse member extending from the second rod, the second rod having a second sensor operably connected thereto;*

*receiving data via a microchip connected to the first and second sensors; and*

*providing the data to a user to facilitate intraoperative adjustments to the orthopaedic device by the user.*

*20. The method of claim 19, wherein the first portion of bone is a vertebra and the orthopaedic device is a spinal fusion rod assembly.*

*21. The method of claim 19, wherein the data is configured to facilitate intraoperative adjustments to the orthopaedic device to achieve one of a desired stress, strain and pressure applied to the first portion of bone via the orthopaedic device.*

*22. The method of claim 19, wherein the data includes one of a stress, strain and pressure applied to the orthopaedic device.*

*23. A method of orthopaedic surgery, comprising:*

*attaching a spinal fixation member to a bone via a transverse member extending therefrom, the spinal fixation member including a sensor operably connected thereto to monitor the spinal fixation member; and*

*intraoperatively receiving data from the sensor via a microchip connected to the sensor, the data corresponding to a desired intraoperative adjustment of the spinal fixation member.*

*24. The method of claim 23, wherein the spinal fixation member is a spinal fusion rod assembly.*

*25. The method of claim 23, wherein the spinal fixation member includes two rods configured to be attached to opposing sides of the bone.*

*26. The method of claim 23, wherein the sensor detects one of stress, strain and pressure applied to the bone.*

* * * * *